(12) United States Patent
Boot et al.

(10) Patent No.: US 9,573,434 B2
(45) Date of Patent: Feb. 21, 2017

(54) TRAILER AND CHASSIS DESIGN FOR MOBILE CORE SCANNING SYSTEM

(71) Applicant: GE Energy Oilfield Technology, Inc., Houston, TX (US)

(72) Inventors: John C. Boot, Atlanta, GA (US); Thomas G. Szudajski, Houston, TX (US); Mongquy V. To, Houston, TX (US)

(73) Assignee: GE ENERGY OILFIELD TECHNOLOGY, INC., Houston, TX (US)

( * ) Notice: Subject to any disclaimer, the term of this patent is extended or adjusted under 35 U.S.C. 154(b) by 0 days.

(21) Appl. No.: 14/587,615

(22) Filed: Dec. 31, 2014

(65) Prior Publication Data
US 2016/0185174 A1    Jun. 30, 2016

(51) Int. Cl.
| | | |
|---|---|---|
| *B60G 11/27* | (2006.01) | |
| *B60P 3/073* | (2006.01) | |
| *B60G 3/01* | (2006.01) | |
| *G01N 33/24* | (2006.01) | |
| *B60S 9/12* | (2006.01) | |
| *B60D 1/00* | (2006.01) | |
| *B60S 9/02* | (2006.01) | |

(52) U.S. Cl.
CPC ............... *B60G 11/27* (2013.01); *B60D 1/00* (2013.01); *B60G 3/01* (2013.01); *B60P 3/073* (2013.01); *B60S 9/02* (2013.01); *B60S 9/12* (2013.01); *G01N 33/24* (2013.01); *B60G 2202/24* (2013.01); *B60G 2300/04* (2013.01); *B60G 2500/10* (2013.01); *G01N 2201/0216* (2013.01); *G01N 2201/10* (2013.01)

(58) Field of Classification Search
CPC .................................. B60S 9/12; B60G 11/27
See application file for complete search history.

(56) References Cited

U.S. PATENT DOCUMENTS

| | | | | |
|---|---|---|---|---|
| 3,704,898 A | * | 12/1972 | Schmidt ............... | B60G 17/052 267/256 |
| 3,746,369 A | * | 7/1973 | Neff .................... | B62D 53/0864 280/438.1 |
| 4,977,586 A | * | 12/1990 | Curry .................. | G01M 17/028 378/56 |
| 5,153,899 A | * | 10/1992 | Curry .................. | G01N 23/185 378/58 |

(Continued)

*Primary Examiner* — Kevin Hurley
(74) *Attorney, Agent, or Firm* — Hogan Lovells US LLP

(57) ABSTRACT

A chassis that supports a scanning system that images core samples from a wellbore. The chassis provides a mounting base for the scanning system for transportation of the scanning system, and also while the scanning system is in use and stationary. A suspension system mounts between the chassis and wheels that facilitate transportation of the chassis. The suspension system isolates the scanning system from shock and vibration encountered by the wheels while transporting the chassis and scanning system. In an example the chassis is a trailer, and which is pulled by a tractor. Legs can telescope downward from the chassis and against the surface on which the chassis is disposed. Airbags are strategically located within the chassis that absorb the vibration and thereby isolate the scanning system from the shock and vibration. Locations of the airbags include paths of force transmission between the wheels and the trailer.

20 Claims, 9 Drawing Sheets

(56) References Cited

U.S. PATENT DOCUMENTS

| | | | |
|---|---|---|---|
| 5,318,123 A | 6/1994 | Venditto et al. | |
| 5,360,066 A | 11/1994 | Venditto et al. | |
| 5,386,875 A | 2/1995 | Venditto et al. | |
| 5,409,251 A * | 4/1995 | Thorndyke | B60S 9/12 280/475 |
| 5,509,687 A * | 4/1996 | Thorndike | B60S 9/12 254/419 |
| 7,082,185 B2 * | 7/2006 | Freifeld | G01N 23/04 250/255 |
| 7,866,386 B2 | 1/2011 | Beer et al. | |
| 8,327,932 B2 | 12/2012 | Karanikas et al. | |
| 8,562,078 B2 | 10/2013 | Burns et al. | |
| 8,636,323 B2 | 1/2014 | Prince-Wright et al. | |
| 8,657,000 B2 | 2/2014 | Willingham et al. | |
| 8,725,477 B2 | 5/2014 | Zhang et al. | |
| 2005/0127620 A1 * | 6/2005 | Amundson | B60S 9/12 280/6.153 |
| 2013/0182819 A1 * | 7/2013 | Dvorkin | G01N 23/046 378/5 |
| 2015/0044004 A1 * | 2/2015 | Pham | B65D 88/32 414/332 |

* cited by examiner

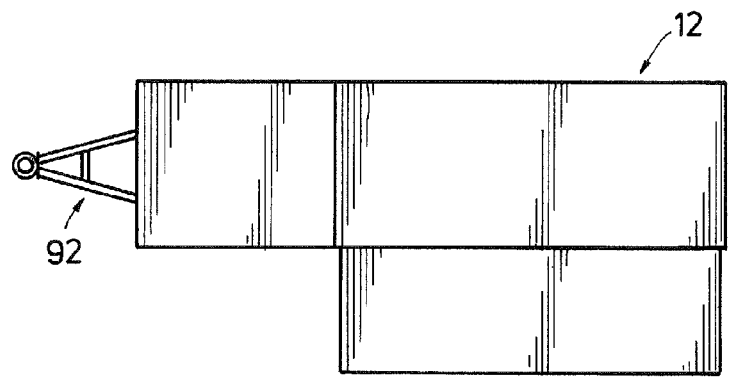
FIG.6
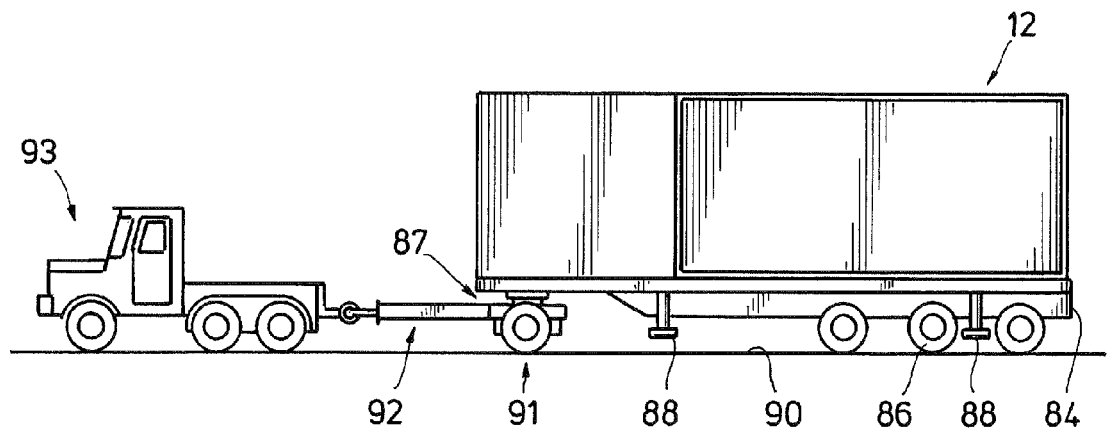
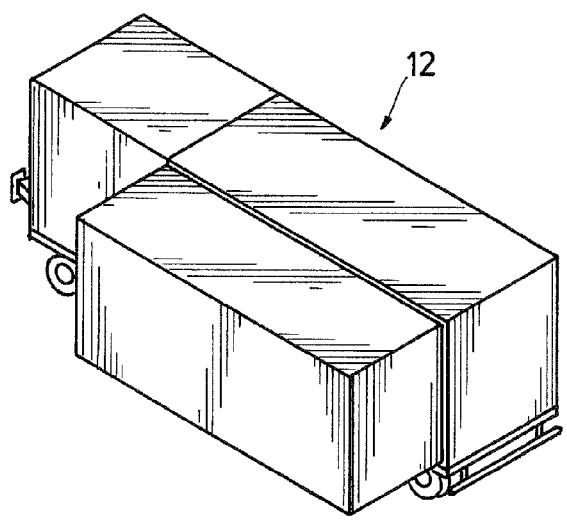

TRAILER AND CHASSIS DESIGN FOR MOBILE CORE SCANNING SYSTEM

BACKGROUND OF THE INVENTION

1. Field of Invention

The present disclosure relates in general to a method and system for analyzing a core sample from a wellbore. More specifically, the present disclosure relates to a trailer and chassis design that isolates a core scanning system from shock and vibration.

2. Description of Prior Art

Various techniques are currently in use for identifying the presence of hydrocarbons in subterranean formations. Some techniques employ devices that emit a signal from a seismic source, and receive reflections of the signal on surface. Others involve disposing logging devices downhole in a wellbore intersecting the subterranean formation, and interrogating the formation from within the wellbore. Example downhole exploration devices include seismic tools that can transmit and receive seismic signals, or ones that simply receive a seismic signal generated at surface. Other devices collect and sample fluid from within the formation, or from within the wellbore. Nuclear tools are also employed that direct radiation into the formation, and receive radiation that scatters from the formation. Analyzing the scattered radiation can provide information about fluids residing in the formation adjacent the wellbore, the type of fluid, and information about other materials next to the wellbore, such as gravel pack.

Logging downhole also is sometimes done while the wellbore itself is being drilled. The logging devices are usually either integral with a drill bit used during drilling, or on a drill string that rotates the drill bit. The logging devices typically are either nuclear, seismic, can in some instances optical devices. In some instances, a core is taken from the wellbore and analyzed after being retrieved to the surface. Analyzing the core generally provides information about the porosity and/or permeability of the rock formation adjacent the wellbore. Cores are generally elongated cylindrical members and obtained with a coring tool having an open barrel for receiving and retaining the core sample.

SUMMARY OF THE INVENTION

Disclosed herein is an example of a system for analyzing a core sample which includes a chassis, a core sample imaging device on the chassis, wheels coupled to the chassis, and a suspension system for absorbing shock and vibration that comprises an air bag assembly mounted in a path of force transmission between the wheels and the chassis. The system may further include a leg that telescopes from the chassis into supporting force against a surface on which the wheels are in contact. This example may further have an air bag assembly in the leg for absorbing shock and vibration. In an alternative, the system further includes a dolly assembly coupled to and supporting an end of the chassis, wherein the dolly assembly has a base that couples to the chassis, wheels coupled to the base, and an airbag system mounted on the base and in a path of vibrational force between the wheels and the chassis and that is for absorbing shock and vibration. Optionally further included with this example is a frame that extends forward from the base and has a pivoting coupling that selectively couples to a tractor rig, wherein the pivoting coupling isolates shock and vibration in the tractor rig from the chassis and from the core sample imaging device. A trailer may alternatively be provided on the chassis for housing the core sample imaging device. In this embodiment, the chassis, trailer, and core sample imaging device define a mobile unit. Further in this embodiment, the mobile unit has an offset center of gravity. The suspension system can isolate vibration acceleration up to about 4.0 G forces during transit and isolates vibrational forces having a frequency of between about 10 Hz to about 15 Hz. The system may optionally further include multiple mobile enclosures on the chassis that are coupled with a connector, so that coupling between mobile enclosures stiffens the chassis.

Another embodiment of a system for analyzing a core sample includes a chassis, a trailer mounted onto the chassis that forms an enclosure, a core sample imaging device supported on the chassis and housed within the enclosure, wheels coupled to the chassis for providing mobility of the trailer thereby defining a mobile unit, a telescoping leg having an end mounted to the chassis, and a system of air bags provided between the wheels and the chassis and in the telescoping leg. The system of air bags can attenuate shock and vibration experienced by the wheels thereby isolating the chassis and the core sample imaging device from the shock and vibration. In an example, the system of air bags resists axial movement between the chassis and the wheels, so that when the mobile unit is accelerated, the chassis is restrained in a generally level orientation. The system can further include a dolly assembly coupled to and supporting an end of the chassis, and a frame that extends forward from the base and has a pivoting coupling that selectively couples to a tractor rig. In one embodiment, the dolly assembly is made up of a base that couples to the chassis, wheels coupled to the base, and an airbag system mounted on the base and in a path of vibrational force between the wheels and the chassis and that is for absorbing shock and vibration, and wherein the pivoting coupling isolates shock and vibration in the tractor rig from the chassis and from the core sample imaging device.

Also provided herein is a method of isolating forces from a core sample analysis system which includes mounting a core sample imaging device supported on a chassis, coupling the chassis to a series of wheels, and isolating the core sample imaging device from shock and vibration experienced by the wheels by disposing air bags between the wheels and the chassis. The method may further include strategically sizing the air bags so that the air bags isolate the chassis from vibrational forces of up to about 4.0 G forces that are experienced by the wheels. In an embodiment the method also includes strategically disposing the air bags so that the chassis remains substantially level when the chassis is accelerated during transportation. The chassis can be transported by coupling the chassis to a dolly having wheels, a base, and a frame that connects to a tractor rig with a pivoting connection. In an embodiment, the pivoting connection attenuations vibration experienced by the tractor rig from being transferred to the dolly or the chassis. The method may further include providing a telescoping leg on a lower side of the chassis, and providing an air bag in the telescoping leg for attenuation vibration propagating within a surface on which the wheels are in contact.

BRIEF DESCRIPTION OF DRAWINGS

Some of the features and benefits of the present invention having been stated, others will become apparent as the description proceeds when taken in conjunction with the accompanying drawings, in which:

FIG. 6 is a side view of an example of a chassis for supporting a mobile enclosure.

Figure 1:
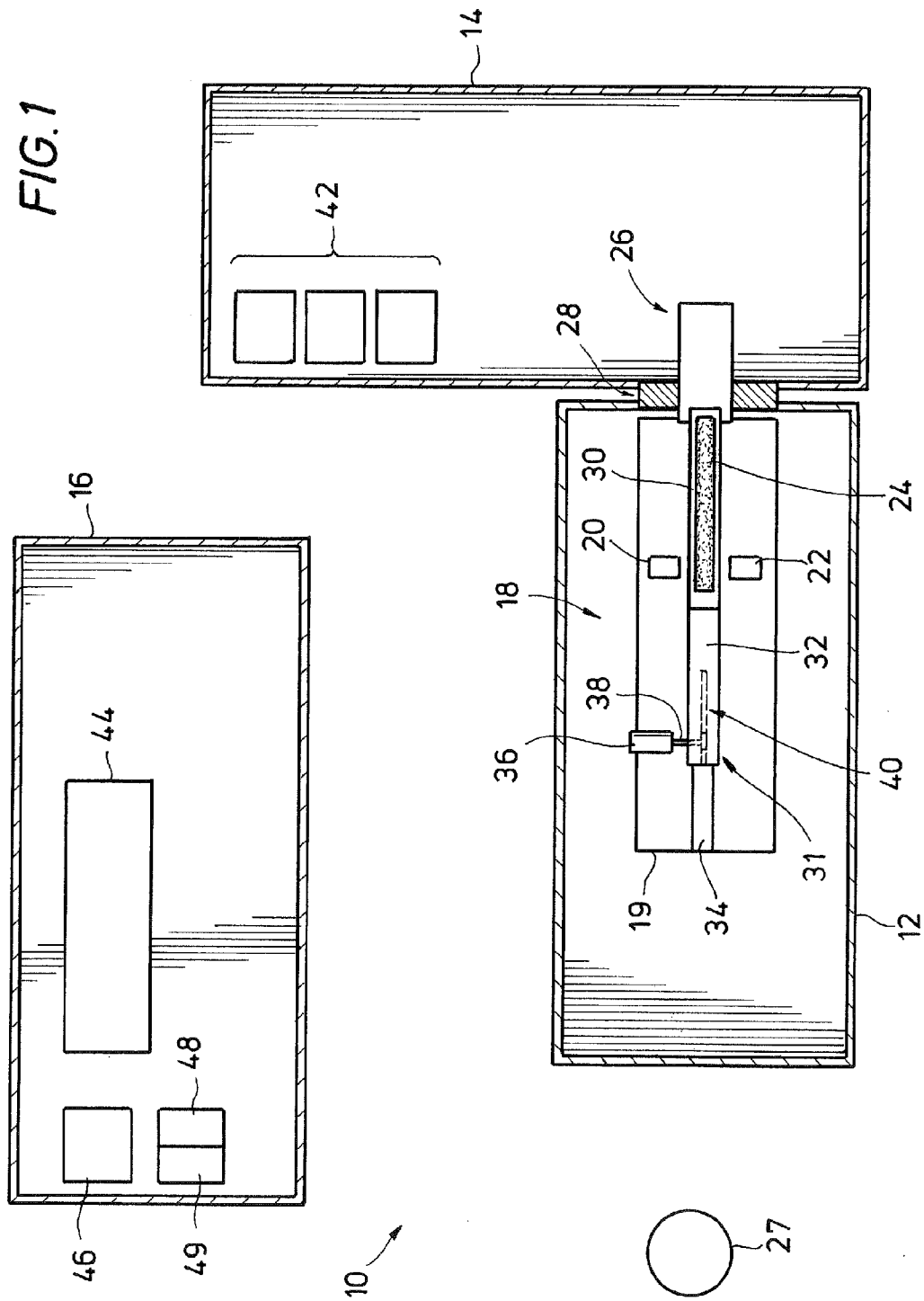
FIG. 1 is a plan partial sectional view of an example of a system for analyzing a core sample.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes, but is not necessarily limited to, +/−5% of the cited magnitude. In an embodiment, usage of the term "substantially" includes, but is not necessarily limited to, +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, them have been disclosed illustrative embodiments and, although specific terms are employed, they are used in a generic and descriptive sense only and not for the purpose of limitation.

Shown in a plan partial sectional view in FIG. 1 is one example of a core analysis system 10, which includes first, second and third mobile enclosures. In the example of FIG. 1, the first mobile enclosure is a scan trailer 12, the second mobile enclosure is a handling trailer 14, and the third mobile enclosure is an analysis trailer 16. In one example, each of the enclosures may be part of a tractor trailer and which are movable by a tractor trailer. Schematically illustrated in the scan trailer 12 is a scan system 18, and substantially all of which is housed within a cabinet 19. In the illustrated example, cabinet 19 is specially designed to shield any radiation within, generated, inherent, or otherwise, from making its way to outside of the cabinet 19. Thus, cabinet 19 is in compliance with 21 C.F.R. 1020.40. Further shown in cabinet 19 is a scan source 20, which in one embodiment includes a device for emitting radiation, such as but not limited to an X-ray, microwave, millimeter wave, etc. A scan receiver 22 is also shown provided within cabinet 19 and combined with scan source 20, in one example, forms a Computed Tomography (CT) scanner.

An elongate and cylindrical core sample 24 is shown axially inserted within scan system 18. Core sample 24 is disposed into scan system 18 through a loading assembly 26, which is shown coupled to one end of the scan system 18 and projecting through an opening in a side wall of handling trailer 14. In an example, core sample 24 is taken from a subterranean formation below system 10, and is retrieved via a wellbore 27 shown adjacent system 10. Thus the wellbore 27 intersects the subterranean formation. Embodiments exist where the system 10 is "onsite" in the field and where the distance between the wellbore 27 to system 10 can range from less than one hundred yards up to five miles, and any distance between. Accordingly, real time analysis while drilling the wellbore 27 can take place within the system 10. Feedback from the analysis can be used by the drilling operator to make adjustments or changes to the drilling operation.

A hatch assembly 28 is schematically illustrated which provides the coupling interface between trailers 12, 14 and includes scaling around the loading assembly 26. While in scan system 18, core sample 24 rests on a core carrier 30. In an example, core carrier 30 is fabricated from a material transparent to X-Rays, and can support the load of the core sample 24 with minimum deflection to maintain the resolution of a stationary scanner. Core carrier 30 is part of a manipulator system 31, which further includes a manipulator arm 32 that telescopingly moves along a manipulator base 34. As shown, an end of manipulator arm 32 distal from manipulator base 34 couples onto an end of core carrier 30, so that core carrier is basically cantilevered on an end of the manipulator arm 32. Manipulator arm 32 is shown in an extended position over manipulator base 34. Manipulator arm 32 axially moves with respect to manipulator base 34 via a motor 36 shown having a shaft 38 that couples to manipulator arm 32. In one example, motor 36 is a linear direct current motor. A gear (not shown) on an end of shaft 38 distal from motor 36 engages a gear rack 40 that is provided on manipulator arm 32. Accordingly, selectively operating motor 36 urges manipulator arm 32, core carrier 30 and core sample 24 in an axial direction with respect to scan source 20. Moving manipulator arm 32 into a retracted position onto manipulator base 34 positions the entire length of core sample 24 in scan system 18, so that all of core sample 24 may be analyzed by the scan system 18. In one example, the scan source 20 and scan receiver 22 orbit around the core sample 24 and so that when in combination of axial movement of core sample 24 within system 18, a helical scan is taken of core sample 24. Further optionally, motor 36, or additional motors not shown, may manipulate and selectively move manipulator arm vertically and/or laterally to thereby better position core sample 24 into a designated orientation and/or spatial position during the scanning process.

Further shown in FIG. 1 are a series of work surfaces 42 provided within handling trailer 14. In one example of operation, before or after core sample 24 is scanned, it may be broken into sections for further analysis and analyzed on surfaces 42. Examples of the surfaces 42 include a crusher, sample divider, and mortar grinder. Additional analysis may take place within analysis trailer 16. Schematically illustrated within analysis trailer 16 are a variety of analysis equipment such as, but not limited to, scanners and spectrometers. One such analysis equipment is a nanotom 44, which can include a scanning system for scanning the internals of core sample 24, or parts of the core sample. Further analysis equipment in the analysis trailer 16 may be a laser induced spectroscope 46, a Raman spectroscope 48, and near infrared spectroscope 49. It will be understood that alternate embodiments may include more trailers or fewer trailers. For example, an appropriately sized scan system 18 may allow loading assembly 26 to be in scan trailer 12 without projecting through an opening in the trailer and without a hatch assembly 28. A further embodiment may provide work surfaces 42 in the same trailer as the analysis equipment, or the analysis equipment may be contained in handling trailer 14. In yet a further embodiment, scan system 18, loading assembly 26, work surfaces 42 and analysis equipment (e.g., nanotom 44, spectroscopes 46, 48, 49, or others) are all contained in one trailer.

Figure 2:
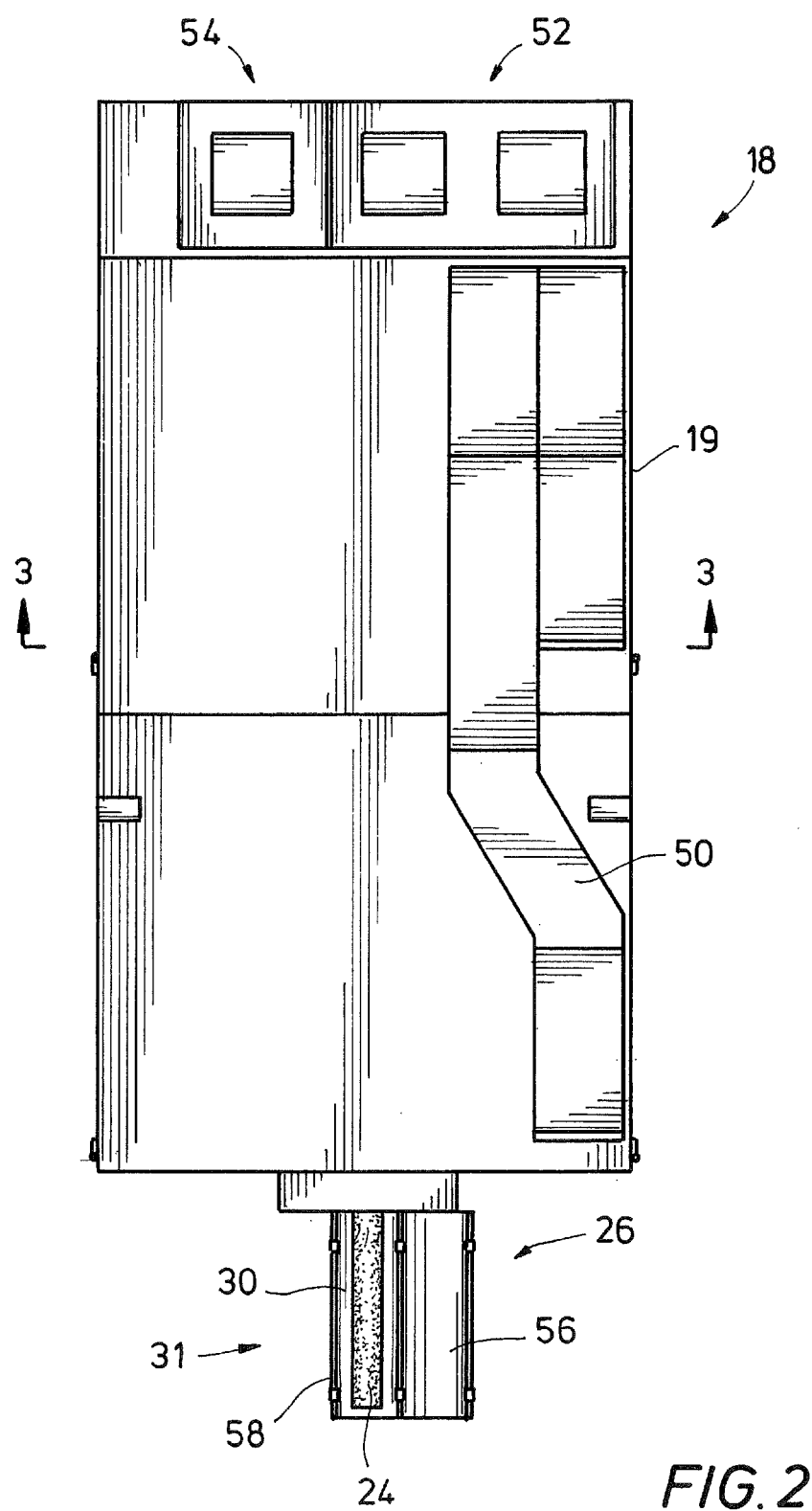
FIG. 2 is an overhead view of an example of a cabinet for shielding radiation and conditioning a scanning unit for a core sample.

Referring now to FIG. 2, shown in an overhead view is an example of the scan system 18 and an upper surface of cabinet 19. Further illustrated in this example is a conditioning vent 50 on an upper end of the cabinet 19, where conditioning vent 50 provides a path for airflow and that is used in conditioning the inside of the cabinet 19, while blocking the leakage of any radiation from cabinet 19. An advantage of the conditioning vent 50 is that conditioned air at proper temperature and humidity may be injected into the inside of cabinet 19 so that the sensitive devices housed within the cabinet 19 may be maintained in proper operating conditions to ensure normal operating functionality. In an example, operational conditions require maintaining a substantially constant temperature within the cabinet 19. In one embodiment, the temperature variation in the cabinet 19 is kept of within 2 degrees C. of a designated temperature. An advantage of the device described herein is that the temperature in the cabinet 19 can be maintained within the designated range in spite of substantial air replacement. Air replacement in the cabinet 19, due to the loading mechanism operation, maintains temperature uniformity across the scanner frame and rotary element. In one example, the volumetric rate of air replacement is at least about 4 m$^3$/min. A power distribution panel 52 is shown provided at an aft end of cabinet 19, and which includes buses (not shown) and other devices for distributing power through cabinet 19 into scan system 18. A control panel 54 is shown adjacent power distribution panel 52 and includes hardware and software for managing control of the operation of the systems house within cabinet 19. Projecting outward past the forward end of cabinet 19 is the loading assembly 26 in an open configuration. In the illustrated example, the loading assembly 26 includes a loading cover 56 and loading basin 58, where the loading cover 56 is shown swung open from a loading basin 58. As shown the core sample 24 has been inserted into open loading assembly 26 and onto the core carrier 30. As will be described in more detail below, safety features are included with the system that prevent operation of the manipulator system 31 when the loading assembly 26 is in the open position of FIG. 2.

Figure 3:
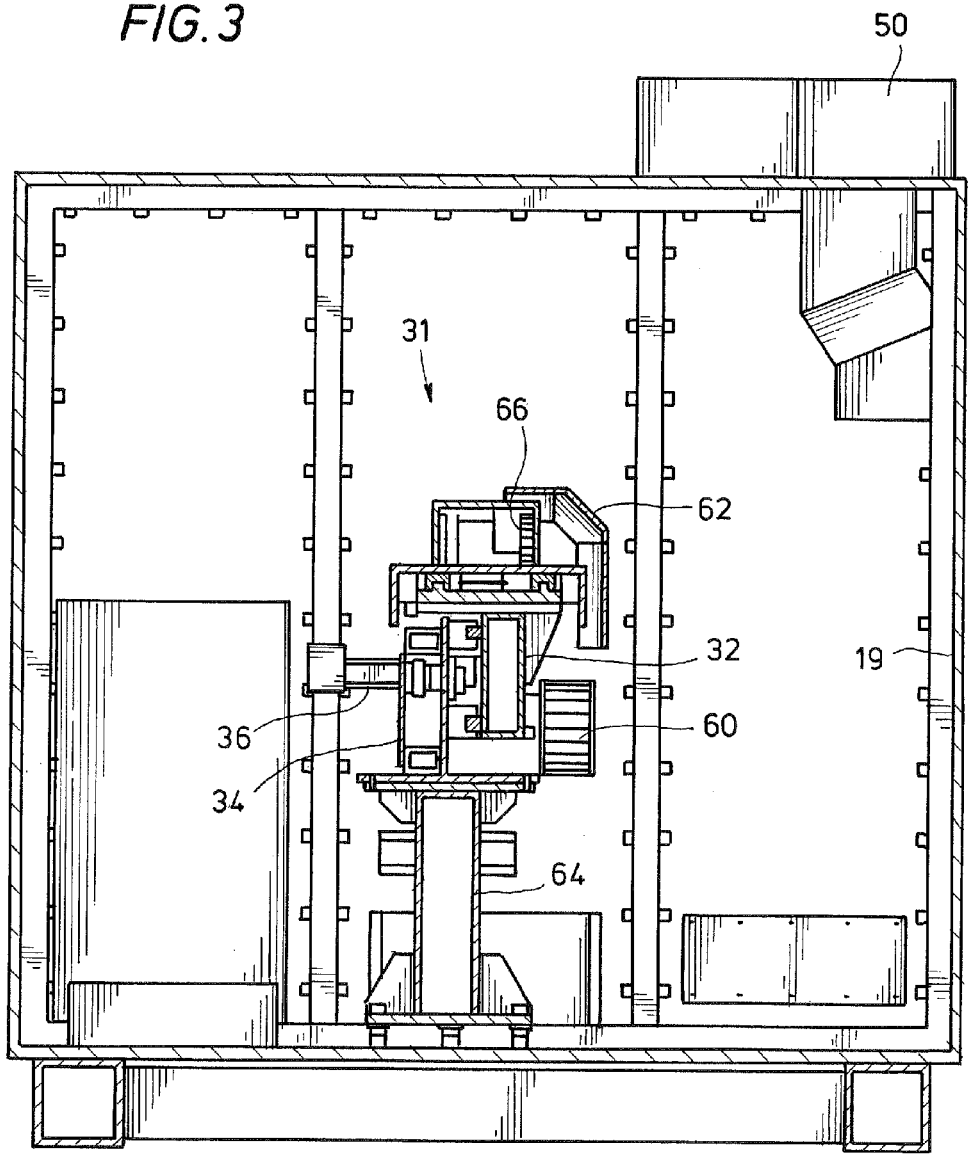
FIG. 3 is an axial sectional view of the cabinet of FIG. 2 and taken along lines 3-3.

FIG. 3 shows an example of the cabinet 19 in a sectional view and taken along lines 3-3 of FIG. 2. This view which is taken along the axial portion of manipulator system 31 shows one example of a wiring track 60; which has cross members for organizing the control and power wires needed for use in the scan system 18 and as the manipulator arm 32 axially moves with respect to manipulator base 34. Wiring track 60 maintains the wires in a designated location and position with use of wiring track 60 during operation of the manipulator system 31. Further in the example of FIG. 3 is a shroud 62 shown mounted on an upper end of manipulator system 31 and which covers a portion of the upper end and shields components within the manipulator system 31. Manipulator base 34 (and thus manipulator arm 32) is supported on a vertical mounting pedestal 64, which has a generally rectangular cross section along its axis, and has a lower end mounted on the floor of cabinet 19. Shown housed within shroud 62 is a wiring bus 66 which extends axially along the manipulator assembly.

Figure 4:
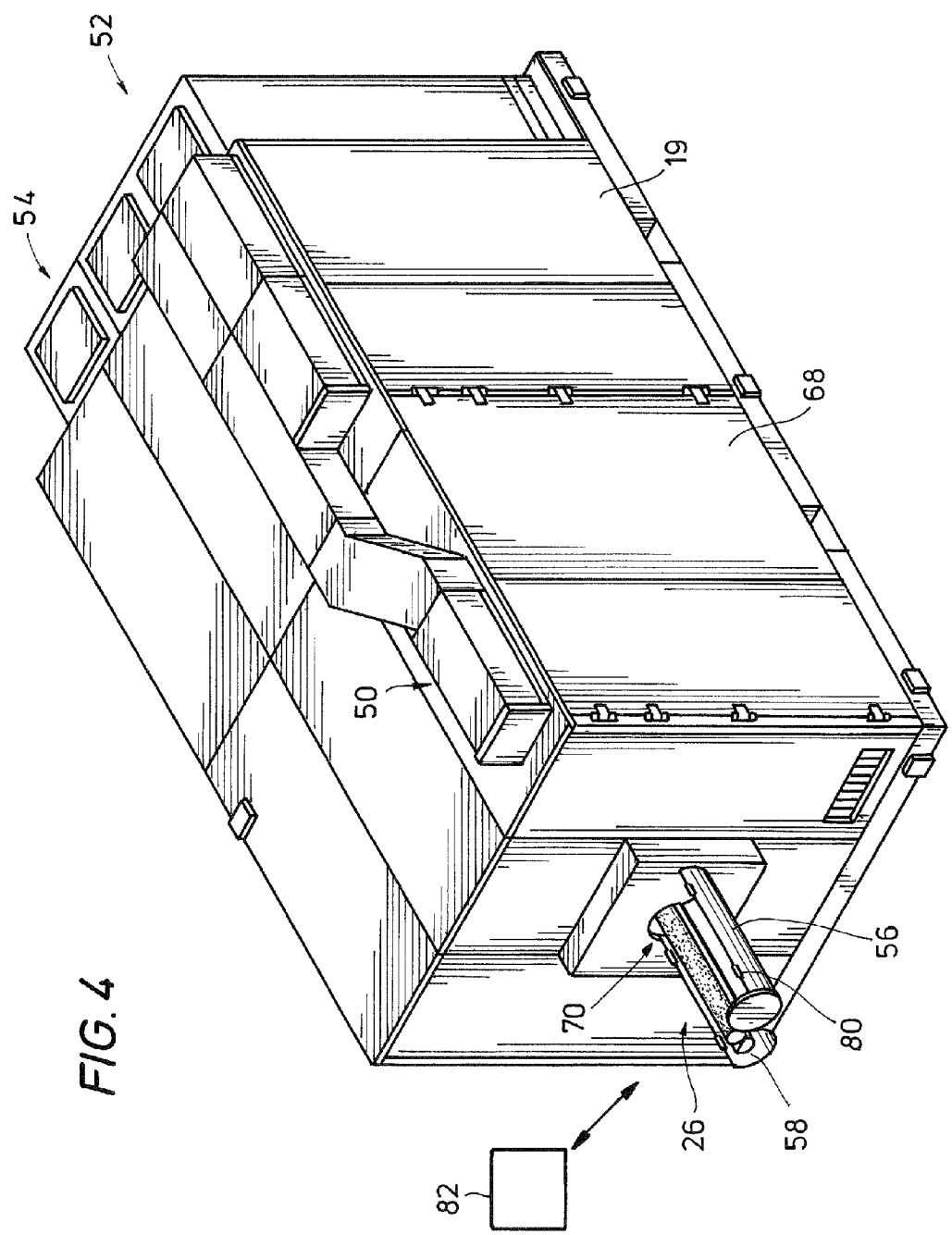
FIG. 4 is a perspective view of the cabinet of FIG. 2.

FIG. 4 provides in perspective view of one example of the cabinet 19 and having hinged panel 68 along its outer surface. As indicated above, the structure of cabinet 19 is in compliance with 21 C.F.R. 1020.40. Thus proper protective shielding and interlocking is provided in the panel 68 and along the hinged interface. An additional safety feature is a door assembly 70 which includes a barrier (not shown) that slides axially across the opening shown at the base of the loading assembly 26 and in a forward wall of cabinet 19. The barrier thus provides a radiation shield from the inside to the outside of cabinet 19 while still allowing core sample loading in compliance with 21 C.F.R. §1020.40.

Figure 5:
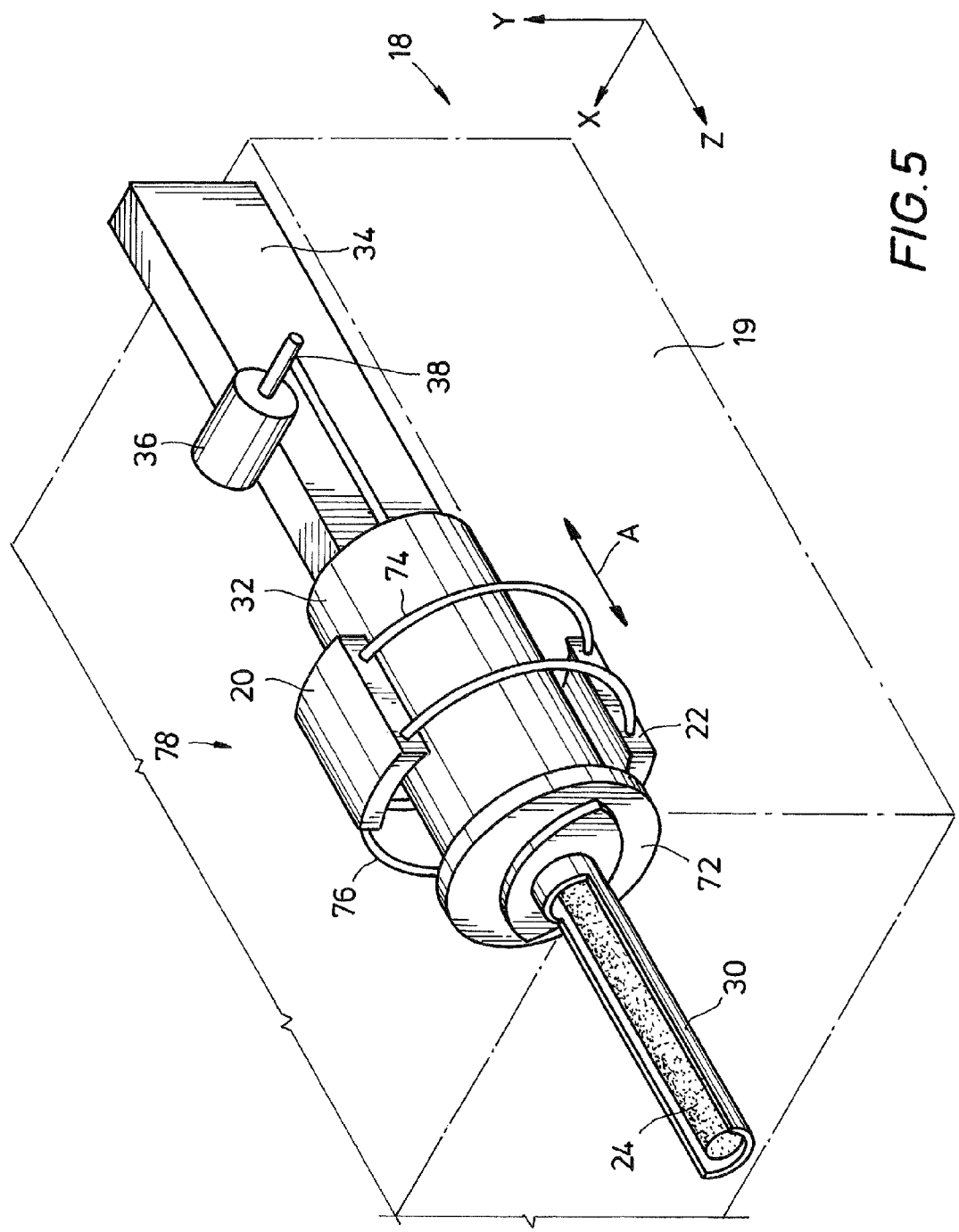
FIG. 5 is a perspective view of the cabinet of FIG. 2 in partial phantom view and an example scanning unit in the cabinet.

An example of the manipulator assembly within cabinet 19 is illustrated in perspective view in FIG. 5, and where cabinet 19 is shown in a partial phantom view. In this embodiment, a rearward end of manipulator base 34 is supported on a rearward end of cabinet 19; manipulator base 34 extends axially away from the rearward wall of cabinet 19 with the manipulator arm 32 axially sliding on manipulator base 34. Motor 36 is shown oriented generally perpendicular to an axis of manipulator arm 32 and manipulator base 34, and couples to manipulator arm 32 by shaft 38. Further illustrated is how the core carrier 30 couples to a mounting plate 72; where mounting plate 72 is a generally circular and planar member that mounts on a forward end of manipulator arm 32. In one embodiment, this member along with an extended tunnel provides the seal that inhibits excessive air flow during the loading process.

Axial movement, as shown by the double headed arrow A, of core sample 24 is accomplished via motor 36. X, Y, and Z axes are illustrated to define an example coordinate system for the purposes of reference herein. While not limited to this coordinate system, the axes depict axial movement of any object, such as the core sample 24, to be along the Z axis, vertical movement to be along the Y axis, and lateral movement to be along the X axis. As indicated above, operation of motor 36 can move core sample 24 along all of these axes. Further shown in FIG. 5 are curved supports 74, 76 that circumscribe manipulator arm 32 and provide a mounting surface for scan source 20 and scan receiver 22. The combination of the support 74, 76 define a gantry 78 that when rotated puts the scan source 20 and scan receiver 22 at an orbiting rotation around the core sample 24 and provides the scanning capabilities of the scan system 18. As indicated above, the air replacement capabilities provided with cabinet 19 maintains a substantially constant temperature across the gantry 78.

Referring back to FIG. 4, an interlock connector 80 is shown provided on the loading cover 56 and loading basin 58. The interlock connectors 80 thus may recognize when the cover 56 is in the open position of FIG. 4 and in combination with controller 82 may prevent operation of the manipulator assembly. However, the control system associated with the scan system 18 that allows for motion of the manipulator assembly when the cover 56 is in the closed position and interlock connectors are adjacent one another.

Shown in a side view in FIG. 6 is an example of the scan trailer 12 mounted on a chassis 84. Wheels 86 are provided on the chassis 84 for facilitating transportation of the chassis 84 having the scan trailer 12 A suspension system 87 is provided between the wheels 86 and chassis 84, that in one example includes a series of airbags (not shown) for isolating vibration experienced in the wheels 86 from the chassis 84. Further provided with the chassis 84 is a leg 88, which can telescope axially and into supporting contact with a surface 90 on which the chassis 84 is resting. Example surfaces 90 include bare ground, a pad, a road, or other parking surface. Shown extending laterally away from an end of the chassis 84 is an example of a dolly 91, which provides rolling support for a forward portion of the chassis 84. Included with the dolly 91 is a hitch assembly 92 for coupling the chassis 84 to a tractor rig 93 that can selectively pull the chassis 84 (and mounted scan trailer 12) to a designated location. In an alternate embodiment, multiple mobile enclosures (or trailers) are provided on a single chassis 84. A connector (not shown) may adjoin adjacent mobile enclosures, which also helps to stiffen the chassis 84 and reduce its deflection while in transit. An example of a connector is found in U.S. Pat. Nos. 4,599,829 and 5,454,673, which are incorporated by reference herein in their entireties.

More specifically, the suspension system 84, with airbags, can be strategically disposed between the wheels 86 and the chassis 84 so that during transportation of the scan trailer 12, the sensitive scanning equipment housed within the scan trailer 12 is not damaged. Further, airbags can also be selectively disposed within the leg 88, so that when the chassis 84 is stationary and leg 88 is extended to support the chassis 84, the chassis 84, and thus the scan trailer 12, can continue to be isolated from shock/vibration that may be transmitted from the surface 90 to the leg 88. Seismic sources in this instance may emanate from typical wellbore operations, such as hydraulic fracturing.

Advantages of the device disclosed herein include the ability to provide isolation from vibration up to 4.0 g due on/off road transport and through the truck. In one example, these vibrational forces are mitigated down to 0.3 g. A further advantage is to provide isolation from low frequency around the 10 Hz-15 Hz range for suitable operation of scan system 18 and other laboratory analytical equipment in the trailers 12, 14, 16. This isolation can occur while stationary or during transit. The system can also provide leveling while in transit against acceleration, deceleration and turns to prevent tipping over of the off center of gravity loads. In an alternative, the hitch assembly 92 is removable, which can minimize the spacing requirement on site and for container alignment. In another alternative, the air ride suspension and trailer/suspension/tire integration can be variable.

Low frequency vibration at the natural frequency of the trailer while stationary at the drilling site can be mitigated. In one embodiment a site leveling, stabilizing and isolation system is included, which provides support to ensure the equipment is leveled for suitable core loading despite the severely uneven center of gravity. A separate air bag leveling system can optionally be included to balance the off center of gravity during transit incidents such as body dive, acceleration/deceleration. An additional optional airbag isolation system can be provided below the turntable (not shown) which provides vibration isolation of the containerized equipment from the truck vibration.

Figure 7A:
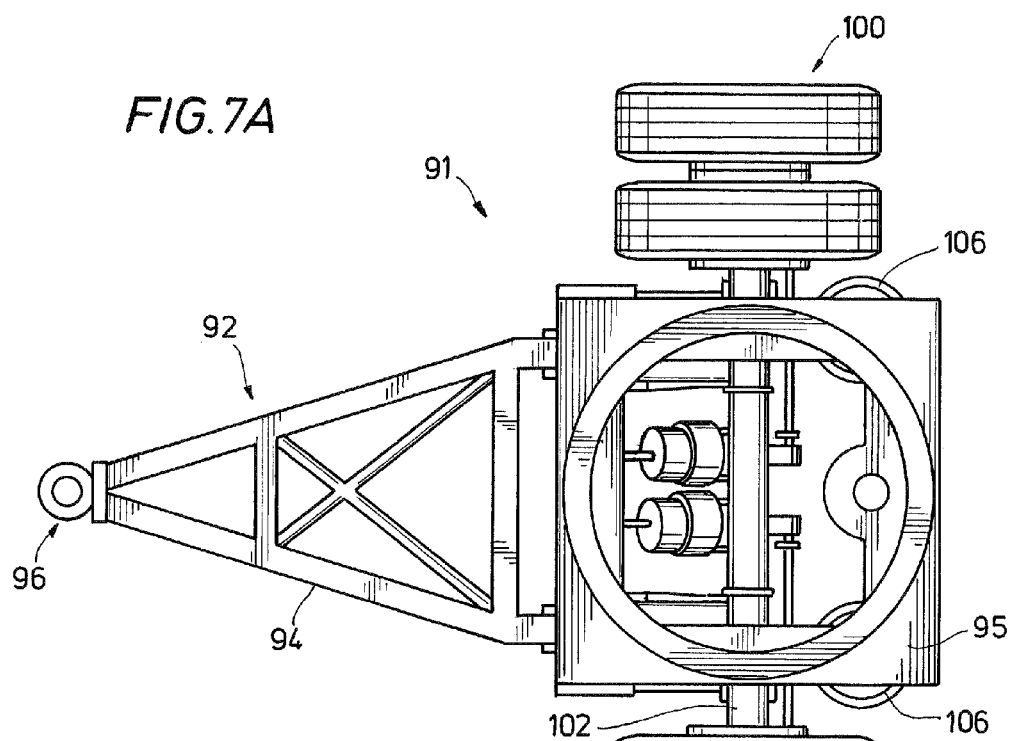
FIGS. 7A and 7B are overhead and side views of an example of a dolly coupled to the chassis of FIG. 6.
Figure 7B:
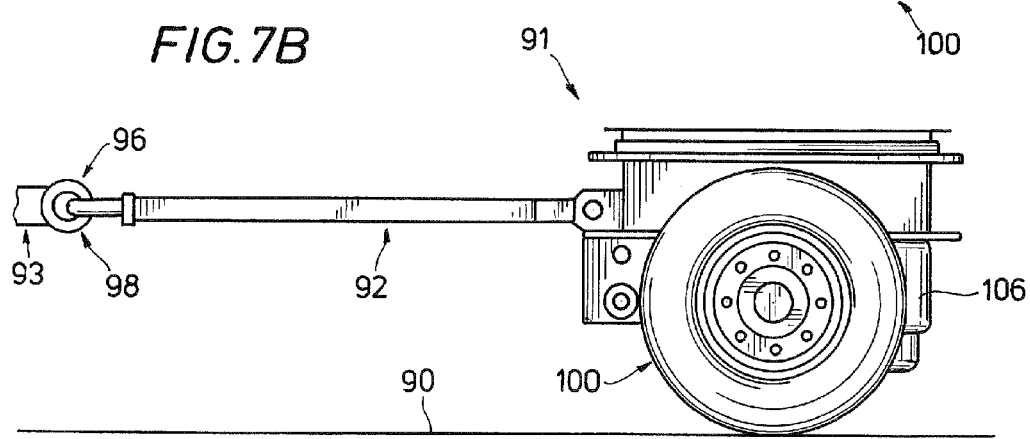

Referring now to FIGS. 7A and 7B, shown respectively in plan and side views is an example of the dolly 91 (FIG. 6). The hitch assembly 92 includes a frame 94 that has an end mounted to a base 95 of the dolly 91. The hitch assembly 92 further includes a pintle ring 96 on an end of the frame 94 distal from the base 95. A pintle hook 98 (FIG. 78) attached to an end of the tractor rig 93 selectively mates with the pintle ring 96 to couple together the tractor 93 and chassis 84 (FIG. 6). The pintle hook 98 and pintle ring 96 selectively transfer an axial force between the two, but can pivot with respect to one another to form a pivoting type connection. An advantage of the dolly 91 and pintle coupling is that the pivoting type connection between the pintle hook 98 and ring 96 attenuate vibrational forces that might otherwise be transferred in a more rigid or fixed coupling. Thus a reduced amount of vibrational forces are transferred from the tractor 93 to the chassis 84. As such, the scan system 18 (FIG. 1) can be isolated from vibrational forces transmitted by the tractor 93. Further illustrated in FIGS. 7A and 7B are wheels 10 that mount on an axle 102 that extends through the base 95 of the dolly 91. Air bags 106 are shown mounted to the base 95 for attenuating vibration experienced by the wheels 100 that may otherwise be transmitted from the wheels 100, thereby isolating the chassis 84 from vibrational forces generated as the wheels 100 travel along the surface 90. Moreover, the air bags 106, in conjunction with other air bags coupled with the chassis 84, can maintain the chassis 84 level, even when the trailer 12 is being accelerated/decelerated, thus preventing "body dive" and other types of tipping that an unsupported trailer could experience.

Figure 8:
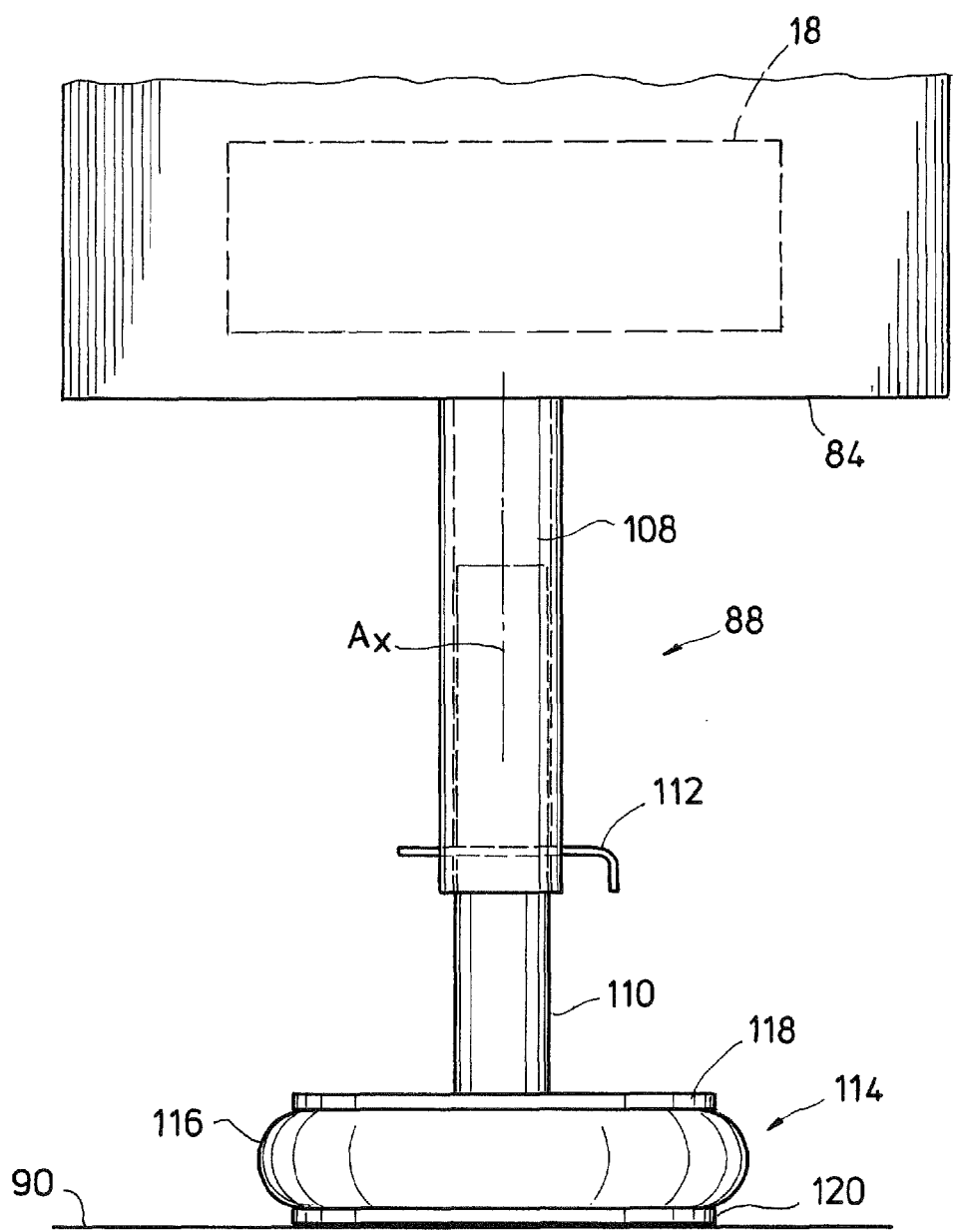
FIG. 8 is a side view of an example of a leg for supporting the chassis of FIG. 6.

FIG. 8 shows in elevational side view an example of a leg 88 attached to a lower end of the chassis 84 and which provides support for the chassis 84. In the example of FIG. 8, the leg 88 includes an upper portion with an end that connects to a lower end of the chassis 84, and a lower portion 110 that inserts into an end of upper portion 108 distal from chassis 84 and that selectively telescopes with respect to the upper portion 108 thereby making both the length of the leg 88 and the elevation of the chassis 84 adjustable. A pin 112 is optionally provided for locking together the upper and lower portions 108, 110 and setting a length of the leg 88. Further included in the example of FIG. 8 is an air bag assembly 114 for isolating the chassis 84 from vibrational forces that might be propagating to or along the surface 90. Example vibrational forces that propagate to/along the surface include those generated by vehicles that may be proximate the chassis 84, as well as from downhole activities, e.g. hydraulic fracturing, formation drilling, perforating, logging, and the like. The air bag assembly 114 thus also isolates the scan system 18 (shown in dashed outline above the chassis 84) from vibrational forces propagating to/along the surface 90. The example air bag assembly 114 includes a membrane 116, which in an example is formed from an elastomeric material that in one embodiment is filled with a fluid (e.g. air, nitrogen, water). Alternatively, membrane 116 could be a substantially solid member, where example materials include an elastomeric material or other vibrational attenuating substance. An upper plate 118 is shown mounted on a lower end of lower portion 110 and rests on an upper portion of membrane 116. Lower plate 120 is shown generally coaxial with upper plate 118 and on a side of membrane opposite upper plate 118. Upper and lower plate 118, 120 as shown are generally transverse to an axis $A_X$ of the leg 88.

Figure 9:
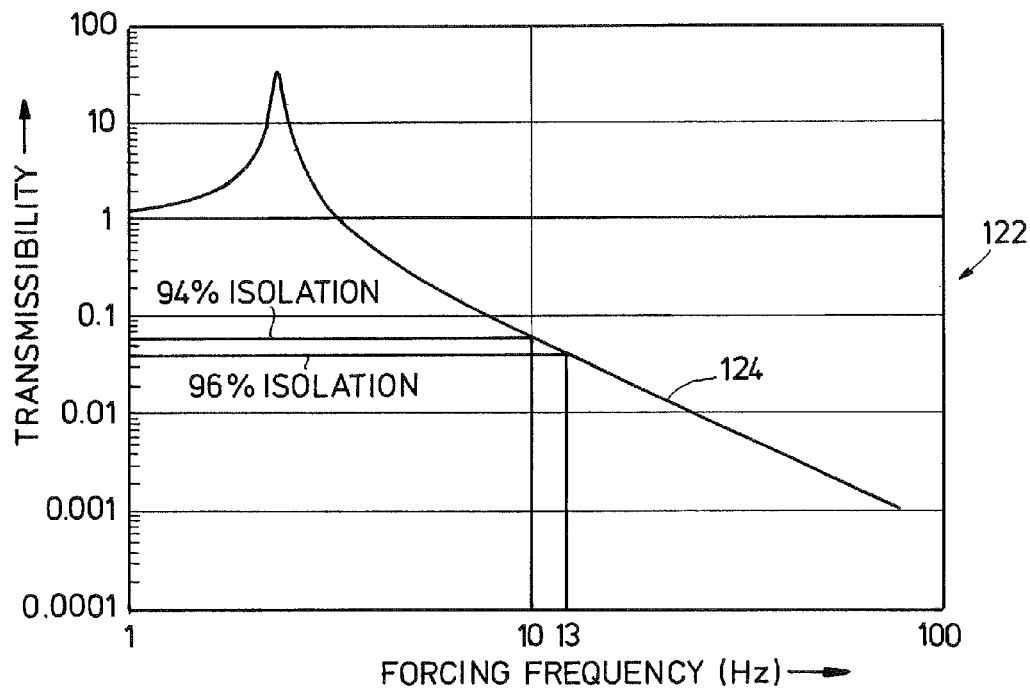
FIG. 9 is a graphical illustration of vibration isolation provided by an example of a suspension system provided with the chassis of FIG. 6.
Figure 10A:
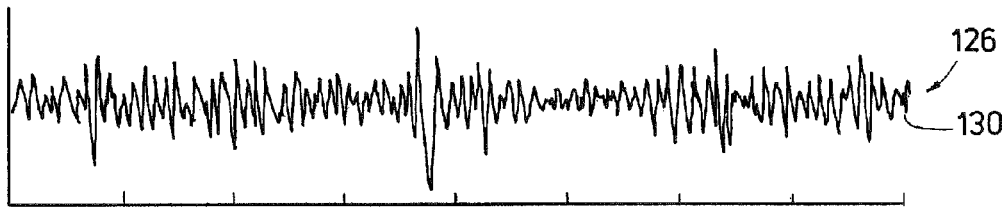
FIGS. 10 A and B are graphical illustrations of vibration absorbed by the chassis of FIG. 6 while being transported.
Figure 10B:
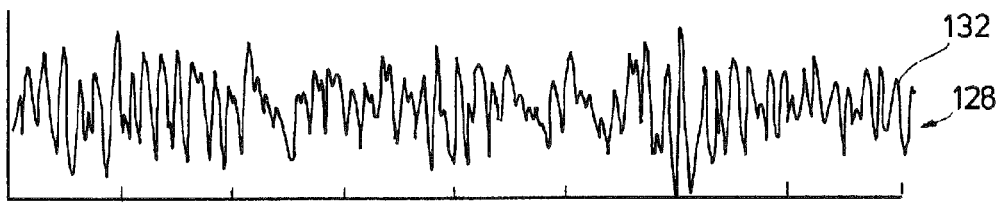

Graphically depicted in the example of FIG. 9 is a plot 122 having a line 124 representing values of vibrational transmissibility (ordinate) across the suspension system 87 with respect to values frequency (abscissa). In the illustrated embodiment, vibration frequencies of interest range from about 10 Hz to about 15 Hz. At these respective frequencies, and as illustrated by line 124, the suspension system 87 (with airbags) provides about 94 to about 96% vibration mitigation. Such mitigation enables the scan system 18, and other associated analytical equipment, to provide accurate readings during use, such as when located at or adjacent a drilling rig (not shown). FIGS. 10A and 1011 are graphical illustrations of plots 126, 128 with lines 130, 132 that represent amounts of vibration absorbed by the chassis 84 (FIG. 6) over time while being transported on a paved surface, such a road formed from asphalt or concrete. The units of the vibration are in gravitational force (G-force) (ordinate) and seconds (abscissa). Plot 126 reflects the vibration the chassis 84 would experience on the example paved surface without the air suspension system 87. Plot represents vibrational forces experienced by the chassis 84 equipped with the suspension system 87 having the air bags (not shown). Clearly illustrated in FIGS. 10A and 10B is that the chassis 84 having the suspension system 87 described herein is subjected to vibrational amounts of less than 0.3 G forces. In contrast, without the suspension system 87, as shown in FIG. 10A, vibrational forces exerted onto the chassis 84 are up to 3 G forces. Accordingly, a 90% reduction of vibrational forces is experienced with the chassis 84 having the suspension system 87, which is unexpected.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. Features of the system described herein provide appropriate trailer height, leveling and trailer dimensions suitable for preparing and loading core samples as well as testing in mobile CT scanning and laboratory analytical equipment on a container whose center of gravity is offset. The present system also provides sufficient spacing between trailers through a modified equipment hitch and tongue design and provide isolation from vibration up to 4 g from transportation (on or off a paved surface), or through the trailer rig. Further, while stationary, the scanning systems provided herein are isolated from low frequency vibrations (e.g. from about 10 hz to about 15 hz) by the above described isolation systems. Moreover, the suspension system associated with the chassis 84 maintains the chassis 84 in a level orientation while being transported, even during episodes of acceleration, deceleration, and directional changes, which limits acceleration forces experienced by the scanning equipment and also maintains the chassis 84 in a stable orientation. These and other similar modifications will readily suggest themselves to those skilled in the art, and are intended to be encompassed within the spirit of the present invention disclosed herein and the scope of the appended claims.

What is claimed is:

1. A system for analyzing a core sample comprising:
a chassis;
a core sample imaging device on the chassis, the core sample imaging device operable to analyze a core sample taken from a subterranean formation;
wheels coupled to the chassis;
a suspension system for absorbing shock and vibration that comprises an air bag assembly mounted in a path of force transmission between the wheels and the chassis; and
a core carrier, the core carrier operable to support the core sample and being moveable in an axial direction between an extended position and a retracted position with respect to a scan source of the core sample imaging device.

2. The system of claim 1, further comprising a leg that telescopes from the chassis into supporting force against a surface on which the wheels are in contact and an air bag assembly in the leg for absorbing shock and vibration.

3. The system of claim 2, further comprising an air bag assembly for leveling the chassis when the chassis is stationary.

4. The system of claim 1, further comprising a dolly assembly coupled to and supporting an end of the chassis, wherein the dolly assembly comprises a base that couples to the chassis, wheels coupled to the base, and an airbag system mounted on the base and in a path of vibrational force between the wheels and the chassis and that is for absorbing shock and vibration.

5. The system of claim 4, further comprising a frame that extends forward from the base and has a pivoting coupling that selectively couples to a tractor rig, wherein the pivoting coupling isolates shock and vibration in the tractor rig from the chassis and from the core sample imaging device.

6. The system of claim 1, further comprising a trailer on the chassis for housing the core sample imaging device.

7. The system of claim 6, wherein the chassis, trailer, and core sample imaging device define a mobile unit.

8. The system of claim 7, wherein the mobile unit has an offset center of gravity.

9. The system of claim 1, wherein the suspension system isolates vibration acceleration up to about 4.0 G forces during transit and isolates vibrational forces having a frequency of between about 10 Hz to about 15 Hz.

10. The system of claim 1, further comprising multiple mobile enclosures on the chassis that are coupled with a connector, so that coupling between mobile enclosures stiffens the chassis and extends ISO certification to the length of the connected enclosures.

11. A system for analyzing a core sample comprising:
a chassis;
a trailer mounted onto the chassis that forms an enclosure;
a core sample imaging device supported on the chassis and housed within the enclosure;
wheels coupled to the chassis for providing mobility of the trailer thereby defining a mobile unit;
a telescoping leg having an end mounted to the chassis;
a system of air bags provided between the wheels and the chassis and in the telescoping leg, wherein the leg has an upper portion and a lower portion and air bags are attached to the lower portion.

12. The system of claim 11, wherein the system of air bags attenuate shock and vibration experienced by the wheels thereby isolating the chassis and the core sample imaging device from the shock and vibration.

13. The system of claim 11, wherein the system of air bags resists axial movement between the chassis and the wheels, so that when the mobile unit is accelerated, the chassis is restrained in a generally level orientation.

14. The system of claim 11, further comprising a dolly assembly coupled to and supporting an end of the chassis, and a frame that extends forward from the base and has a pivoting coupling that selectively couples to a tractor rig, wherein the dolly assembly comprises a base that couples to the chassis, wheels coupled to the base, and an airbag system mounted on the base and in a path of vibrational force between the wheels and the chassis and that is for absorbing shock and vibration, and wherein the pivoting coupling isolates shock and vibration in the tractor rig from the chassis and from the core sample imaging device.

15. A method of isolating forces from a core sample analysis system comprising:
  mounting a core sample imaging device supported on a core carrier of the chassis, the core carrier operable to support the core sample and being movable in an axial direction between an extended position and a retracted position with respect to a scan source of the core sample imaging device, and wherein the core sample imaging device is operable to analyze a core sample taken from a subterranean formation;
  coupling the chassis to a series of wheels; and
  isolating the core sample imaging device from shock and vibration experienced by the wheels by disposing air bags between the wheels and the chassis.

16. The method of claim 15, further comprising strategically sizing the air bags so that the air bags isolate the chassis from vibrational forces of up to about 4.0 G forces that are experienced by the wheels.

17. The method of claim 15, further comprising strategically disposing the air bags so that the chassis remains substantially level when the chassis is accelerated during transportation.

18. The method of claim 15, further comprising transporting the chassis by coupling the chassis to a dolly having wheels, a base, and a frame that connects to a tractor rig with a pivoting connection.

19. The method of claim 18, wherein the pivoting connection attenuations vibration experienced by the tractor rig from being transferred to the dolly or the chassis.

20. The method of claim 18, further comprising providing a telescoping leg on a lower side of the chassis, and providing an air bag in the telescoping leg for attenuation vibration propagating within a surface on which the wheels are in contact.

* * * * *